Figure 1:
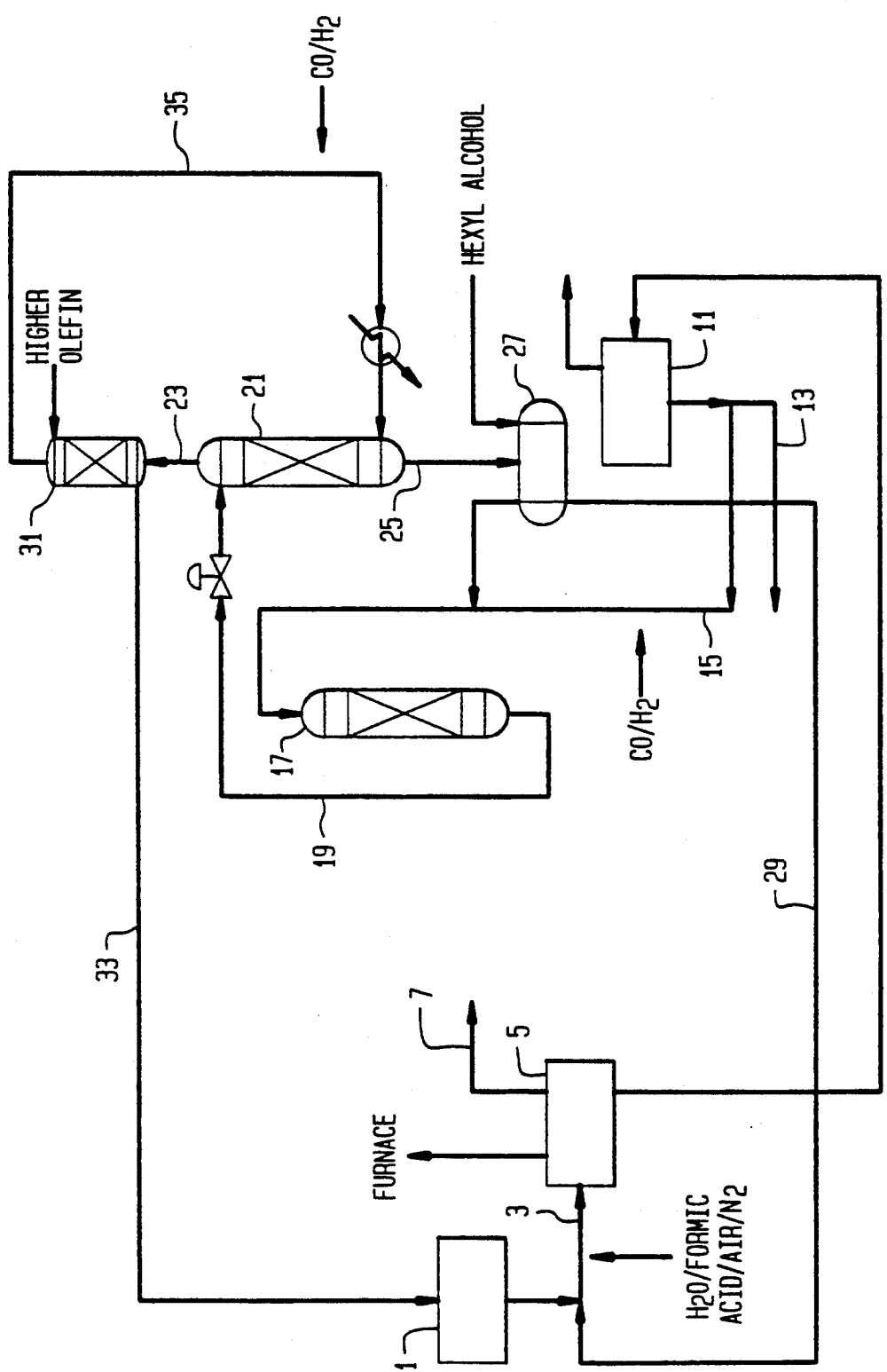

United States Patent [19]
Roussel et al.

[11] Patent Number: 5,321,168
[45] Date of Patent: Jun. 14, 1994

[54] ACTIVATION OF COBALT PREFORMER CATALYST FOR OXO PROCESS

[75] Inventors: Patricia B. Roussel; William H. Summerlin, both of Baton Rouge, La.

[73] Assignee: Exxon Chemical Patents Inc., Linden, N.J.

[21] Appl. No.: 122,859

[22] Filed: Sep. 16, 1993

[51] Int. Cl.⁵ .................. C07C 27/22; C07C 29/141; C07C 31/125
[52] U.S. Cl. .................................. 568/882; 502/22; 568/451; 568/883
[58] Field of Search .................. 568/883, 882, 451; 502/22

[56] References Cited

U.S. PATENT DOCUMENTS

| | | | |
|---|---|---|---|
| 3,255,259 | 6/1966 | Mertzveiller et al. | 568/882 |
| 4,147,660 | 4/1979 | Yamauchi et al. | 502/22 |
| 4,255,279 | 3/1981 | Spohn et al. | 252/413 |
| 4,400,299 | 8/1983 | Lagace et al. | 252/413 |
| 4,404,119 | 9/1983 | Lagace et al. | 568/451 |
| 5,237,105 | 8/1993 | Summerlin | 568/451 |

FOREIGN PATENT DOCUMENTS

| | | | |
|---|---|---|---|
| 101794 | 8/1979 | Japan | 502/22 |
| 160048 | 6/1990 | Japan | 502/22 |

Primary Examiner—Joseph E. Evans
Attorney, Agent, or Firm—John J. Mahon

[57] ABSTRACT

Noble metal or other preformer catalysts used to convert cobalt salts to hydrido cobalt carbonyl for use in the oxonation of olefins are activated or regenerated by treatment with $H_2O$ at 120° to 170° C., 13.78 MPa (2,000 psig) to 31.00 MPa (4,500 psig) for 2–50 hours.

5 Claims, 2 Drawing Sheets

ACTIVATION OF COBALT PREFORMER CATALYST FOR OXO PROCESS

This invention relates to the oxo process for preparing oxo alcohols by the hydroformylation of olefins. More particularly, this invention relates to an improvement in the use of a preformer catalyst used to effect the conversion of cobalt salts to the active cobalt species in the cobalt catalyzed hydroformylation of olefins.

The oxo process is the commercial application of the hydroformylation reaction for making higher alcohols from olefin. In the cobalt oxo process, an olefin reacts with CO and $H_2$ (syn gas) at elevated temperature in the presence of a cobalt carbonyl catalyst to produce a hydroformylation reaction product which is subsequently decobalted or demetalled to produce a crude product mixture of aldehydes, alcohols, acetals, formates, unreacted olefins and secondary products. Subsequent hydrogenation steps provide the desired finished alcohol products commonly referred to as oxo alcohols (alcohols produced by an oxonation reaction).

One aspect of the overall cobalt oxo process involves the preparation of the active cobalt catalyst species which is hydrido cobalt carbonyl, $HCo(CO)_4$. Commercial oxo processes employ a preforming step in which this active cobalt catalyst species is prepared using a noble metal preforming catalyst which is contacted with a cobalt salt, e.g., cobalt formate, to provide the desired $HCo(CO)_4$ species.

This preforming step is disclosed, for example, in U.S. Pat. No. 4,404,119 issued Sep. 13, 1983 to Lagace et al. and in U.S. Pat. No. 4,255,279 issued Mar. 10, 1981 to Spohn et al.

In accordance with the present invention there has been discovered an improvement in the process for preparing oxo alcohols by the cobalt catalyzed hydroformylation of $C_2$ to $C_{17}$ linear or branched monoolefins with subsequent hydrogenation of the hydroformylation reaction product, in which process aqueous solutions of cobalt salts are converted to active hydrido cobalt carbonyl catalyst species in a preformer reactor, the preformer containing (i) preformer metal catalyst of Group IB or VIII of the Periodic Table or (ii) a preformer nonmetallic catalyst selected from the group consisting of activated carbon, ion exchange resins, silica alumina and zeolites, the improvement which comprises activating said preformer catalyst by treating it at a temperature of about 120° C. to 170° C. and at a pressure of about 13.78 MPa (2,000 psig) to 31.00 MPa (4,500 psig) and preferably about 20.67 MPa (3,000 psig), with water or with a mixture of water and hydrogen or a mixture of water and syn gas for a period of about 2–50 hours, whereby the conversion of said cobalt salts to hydrido cobalt carbonyl is improved when such salts are contacted with said treated preformer catalyst.

The relative amounts of water and hydrogen or syn gas are such that the molar ratio is about 3–100 moles of water per mole of gas (either hydrogen or syn gas) with the preferred ratio being 12–25 moles of water per mole of either hydrogen or syn gas.

The present invention is preferably employed in an oxo process in which the olefin is preferably a mixture of linear and branched $C_5$ to $C_{12}$ monoolefins, the hydroformylation typically being carried out at a pressure of 15–30 MPa and a temperature of about 120° to 190° C. Cobalt is present as hydrido cobalt carbonyl in a concentration of from 0.05 to 3.0 wt.%, calculated as metallic cobalt based on olefin feedstock. The synthesis gas ($H_2$ and CO) typically has a $H_2$:CO volume ratio in the range of 0.9:1 to 1.5:1, preferably about 1:1.

Particularly preferred preformer catalysts comprise Group IB and VIII metals such as palladium, platinum or gold. Such catalysts may be supported or unsupported using supports such as silica, alumina, zeolites or activated carbon and other carbonaceous support material. The preferred preformer catalyst for use in the invention is 0.1 to 5 wt. %, e.g., 2 wt. % palladium supported on activated carbon.

While the process of this invention is especially useful for the activation or regeneration of a noble metal catalyst, such as Pd on activated carbon, it is also applicable to the activation and regeneration of preformer catalysts comprising activated carbons, ion exchange resins, silica alumina and zeolites. Suitable zeolites are those having pore diameters of 4 to 12 angstroms. Suitable ion exchange resins are those which contain primary, secondary or tertiary amino groups and are based on polystyrene such as "AMBERLITE IR45" and "DOWEX 4". Such catalysts are disclosed in U.S. Pat. No. 3,855,396 issued Dec. 17, 1974 to Kniese et al. and U.S. Pat. No. 3,929,898 issued Dec. 30, 1975 to Nienburg et al.

The preforming reaction is illustrated by the following equations (1) and (2) in which cobalt formate is the illustrative salt undergoing conversion to HCo $(Co)_4$ and Pd is the illustrative preformer catalyst:

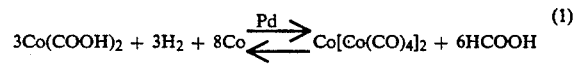  (1)

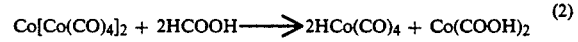  (2)

In the equation (2) hydrido cobalt carbonyl is liberated from $Co[Co(CO)_4]$ by the formic acid which is present as a by-product of the hydroformylation process and also as a result of the preforming reaction shown in equation (1).

In the operation of the oxo process the preformer treats an aqueous feed containing cobalt salt which is obtained from an acid/air demetalling step, such as is disclosed in U.S. Pat. No. 5,237,105, issued Aug. 17, 1993 to Summerlin, or from the cobalt flash stripper bottom, followed by concentration in an evaporator or a flash unit.

The aqueous phase containing the cobalt salts is co-processed over the catalyst with an appropriate organic phase such as an alcohol or mixture of aldehyde/alcohol/hydrocarbon (crude oxo product). The organic phase is present to keep cobalt from depositing on the catalyst surface. Hydrido cobalt carbonyl has low solubility in water, but high solubility in organic materials such as mentioned above. In this two liquid phase process, the product carbonyl is continuously extracted into the organic phase. This effectively drives the reaction to higher levels of conversion and prevents deposition of cobalt on the catalyst.

Once hydrido cobalt carbonyl is extracted into the organic phase, it can form dicobalt octacarbonyl by the following reversible reaction:

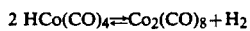

The dicobalt octacarbonyl can also dissociate in the presence of an alcohol as indicated below:

$$3\ Co_2(CO)_8 + 12\ ROH \rightleftharpoons 2(Co(ROH)_6)^{2+} (Co(CO)_4)_2^- + 8\ CO$$

Dicobalt octacarbonyl can also disproportionate with water according to the following reaction:

$$3\ CO_2(Co)_8 \rightleftharpoons 2Co^{2+} (Co(CO)_4)_2^- + 8CO$$

The present invention is applicable for both the initial activation of the preformer catalyst or for the regeneration of a previously used preformer catalyst, thus, the term "activation" as used herein also applies to regeneration of used catalyst.

The activation procedure of this invention may be conducted over a temperature range of about 120° C. to 170° C., preferably at 150° C., and a pressure of 13.78 MPa to 31.00 Mpa (2,000–4,500 psig), preferably at about 20.67 MPa (3,000 psig). The catalyst may be treated with water alone, or preferably, it is treated under these temperature and pressure conditions with a mixture of water and hydrogen, or water and synthesis gas. The water should be cobalt free and may contain very minor amounts, e.g., 0.5–3.0 wt. %, of free formic acid. The treatment should be conducted for a period of about 2–50 hours until the catalyst pores become saturated with water.

Water treatment will be employed in an amount corresponding to 1.0–4.0 LHSV (liquid hourly space velocity), where LHSV is volume/hr. water/volume catalyst. The rate of gas treatment will range from 0–400 GHSV, (gas hourly space velocity) preferably about 50–200 GHSV where GHSV is volume of gas at standard conditions/hr./volume of catalyst. When gas treatment is employed, the gas may be hydrogen or syn gas, a CO/H2 mixture, same as that used in the oxo process. The water stream used for activation is preferably cobalt-free, but it may contain some free formic acid. A useful stream is the evaporator water overhead stream referred to in FIG. 1 which contains formic acid but has no cobalt. The time of treatment is not significant, for fresh catalyst activation it is the time required to fill the dry catalyst pores with water, and for regeneration it is the time required to displace organic material from the pores.

FIG. 1 illustrates an oxo process including a method for removing cobalt values wherein an acid-air cobalt demetalling step is disposed upstream of the stripping step in a Cobalt Flash process. FIG. 1 shows the location of the preformer 17.

FIG. 1 generally depicts a method for removing cobalt values from the crude product of a cobalt-catalyzed hydroformylation reaction formed from an olefinic feedstock having a carbon number in the range C4 to C14, preferably C5 to C7. The crude product typically contains cobalt compounds in addition to an organic hydroformylation reaction product.

An olefin feedstock and syn gas are introduced into oxo reactor 1, wherein hydroformylation is conducted under conventional conditions to yield a crude hydroformylation product containing aldehydes, alcohols, by-products and cobalt catalyst compounds. This crude product is carried via conduit 3 where it is contacted with a stream of oxygen-containing gas, an organic acid and water, thereby producing a substantially cobalt-free organic hydroformylation reaction product and a water soluble cobaltous salt aqueous product, to settling drum or demetalling drum 5. In demetalling drum 5 the substantially cobalt-free crude product is separated from the water soluble cobaltous salt aqueous product. The substantially cobalt-free organic hydroformylation reaction product is diverted overhead via conduit 7 for further downstream treatment such as distillation or hydrogenation. The water soluble cobaltous salt aqueous product is carried via conduit 9 to evaporator 11 which concentrates the water soluble cobaltous salt, thereby producing a concentrated aqueous solution of cobaltous salt and a substantially cobalt-free water containing the organic acid, whereby the concentrated aqueous solution of cobaltous salt is separated from the substantially cobalt-free water containing the organic acid. The substantially cobalt-free water containing the organic acid is recycled via conduit 13 to oxo reactor 1. Whereas the concentrated aqueous solution of cobaltous salt is contacted with an alcohol stream and synthesis gas within conduit 15 before this mixture is passed to preformer reactor 17. In preformer reactor 17 the concentrated aqueous solution of cobaltous salt is converted to a cobalt carbonyl under catalytic conditions. The cobalt carbonyl from preformer reactor 17 is carried via conduit 19 to stripper reactor 21 where it is contacted with a stream of stripping gas at a temperature of not greater than 100° C. and at a pressure below 10.13 bar, the pressure being lower than the decomposition pressure of the cobalt compounds at the contacting temperature, to entrain volatile cobalt compounds in the stripping gas and to generate as bottoms alcohol products and dissolved cobaltous salts; whereby the entrained volatile cobalt compounds are taken out overhead via conduit 23 and the alcohol products and dissolved cobaltous salts are taken out as bottoms via conduit 25. The alcohol products are separated from the dissolved cobaltous salts in settling drum 27. The dissolved cobaltous salts are typically in an aqueous phase, e.g., an aqueous salt product, which can be readily separated from the organic phase, i.e., the alcohol products, by gravity settling. The alcohol products from settling drum 27 are preferably recycled to conduit 15 for mixing with the cobaltous salt upstream of preformer reactor 17. The cobaltous salt from settling drum 27 is preferably recycled via conduit 29 to conduit 3 for further demetalling. Finally, the volatile cobalt compounds from conduit 23 are introduced into absorber 31 where they are contacted with olefinic feedstock, whereby the volatile cobalt compounds are absorbed into the olefinic feedstock and recycled to oxo reactor 1 via conduit 33. Reflux from absorber 31 is returned to stripper reactor 21 via reflux conduit 35. Optionally, syn gas may also be fed into stripper reactor 21 via reflux conduit 35.

Figure 2:
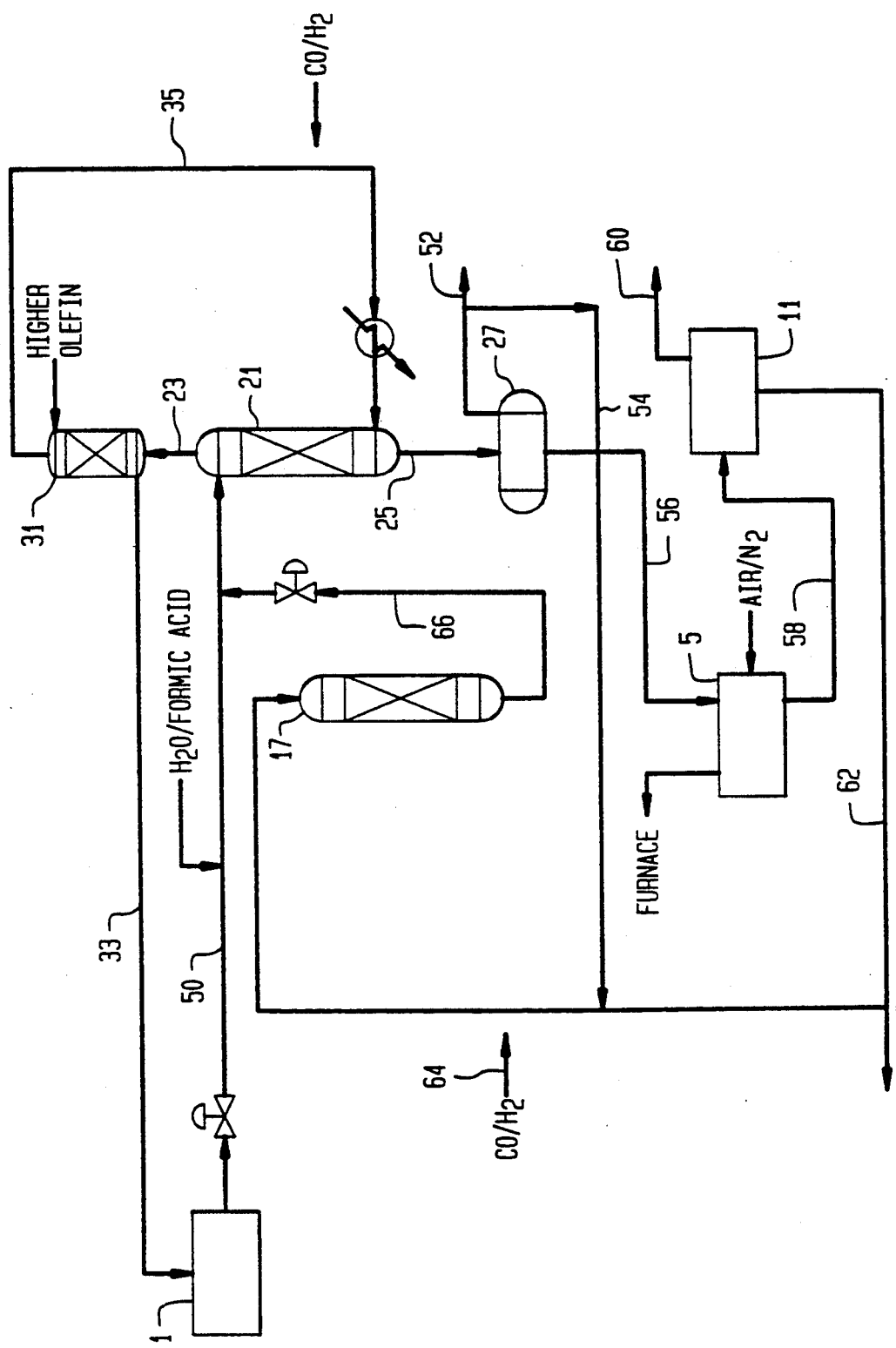

FIG. 2 illustrates a method for removing cobalt values from the crude product of a cobalt-catalyzed hydroformylation reaction formed from an olefinic feedstock having a carbon number in the range of C7–C14, wherein an acid-air cobalt demetalling step is disposed downstream of the stripping step in a Cobalt Flash process.

An olefin feedstock and syn gas are introduced into an oxo reactor 1, wherein hydroformylation is conducted under conventional conditions to yield a crude hydroformylation product containing aldehydes, alcohols, by-products and cobalt catalyst compounds. This crude product is carried via conduit 50 where it is contacted with water and an organic acid, such as formic acid. The treated crude product is thereafter contacted with a stream of stripping gas in stripper reactor 21. The stripping typically occurs at a temperature of not greater than 100° C. and at a pressure below 10.13 bar, the pressure being lower than the decomposition pressure of the cobalt compounds at the contacting temperature, to entrain volatile cobalt compounds in the stripping gas, whereby the entrained volatile cobalt compounds are taken out overhead via conduit 23 and organic hydroformylation reaction products containing water soluble cobaltous salts dissolved therein are taken out as bottoms via conduit 25. The water soluble cobaltous salt is then separated from the organic hydroformylation reaction products by means of settling drum 27. The organic hydroformylation reaction product is then carried via conduit 52 for further downstream treatment such as distillation or hydrogenation. Optionally, a portion of the organic hydroformylation product may be diverted from conduit 52 via conduit 54 and recycled to the preformer reactor 17. The water soluble cobaltous salt is carried via conduit 56 to settling drum or demetalling drum 5 where it is contacted with a stream of oxygen-containing gas, an organic acid and water thereby producing a water soluble cobaltous salt aqueous product. The oxygen should be present in an amount such that the organic acid only sees the water. Thereafter, the water soluble cobaltous salt aqueous product is carried via conduit 58 to evaporator 11 which forms a concentrated aqueous solution of cobaltous salt and a substantially cobalt-free water containing the organic acid. The concentrated aqueous solution of cobaltous salt is then separated from the substantially cobalt-free water containing the organic acid, whereby the substantially cobalt-free water containing the organic acid is recycled via conduit 60 to stripper reactor 21, diverted to the optional water wash treatment step, or diverted to hydrogenation. The concentrated aqueous solution of cobaltous salt is carried via conduit 62 either to preformer reactor 17 or recycled to oxo reactor 1. However, prior to being fed to preformer reactor 17, the concentrated cobaltous salt is contacted with an alcohol stream, a cobalt-free organic hydroformylation reaction product, or a hydrogenation product delivered via conduit 54 and syn gas which is delivered via conduit 64. This mixture is then passed on to preformer reactor 17 where the concentrated aqueous solution of cobaltous salt is converted to a cobalt carbonyl. The cobalt carbonyl is then carried via conduits 66 and 50 to stripper reactor 21. Finally, the volatile cobalt compounds which are carried from stripper reactor 21 via conduit 23 are sent to absorber 31 wherein they are absorbed into the olefinic feedstock and returned to oxo reactor 1 via conduit 33.

EXAMPLE ONE

A 2% Pd on activated carbon catalyst which was being used to convert an aqueous solution of cobalt formate to hydrido cobalt carbonyl in the presence of hexyl alcohol as the organic phase showed a decline in catalyst activity over a 24 day period. For the first 16 days of operation at conditions of 120° C., 5.0 LHSV, 1:1 hexyl alcohol:cobalt formate water containing, 0.55 wt. % cobalt, 20.67 MPa (3,000 psig), 800% excess syn gas (1:1 molar $H_2:CO$), conversion of cobalt formate to hydrido cobalt carbonyl declined from 62.3% to 42.4%. At day 16, temperature was increased to 140° C. to compensate for the deactivation. During the next seven days of operation at the higher temperature, conversion declined from 61.8% to 49.1%. At day 23, residence time in the reactor was increased by lowering liquid hourly space velocity, LHSV, from 5.0 to 2.5. At the longer residence time, conversion of cobalt formate to hydrido cobalt carbonyl was measured as 66.8%.

At this point, the catalyst was given a water/hydrogen activation according to the following procedure. Cobalt water feed and hexyl alcohol feed flows were stopped and clean water was pumped to the reactor containing the 2% Pd on carbon catalyst at a rate of 2.5 LHSV. Syn gas flow was stopped and $H_2$ gas was started at a rate of 100 GHSV. Operating pressure was 20.67 MPA (3,000 psig). For the first three hours the temperature was kept at 150° C. For the next 15 hours temperature was lowered to 140° C.

Following the water/hydrogen activation described above, the catalyst was tested for cobalt formate conversion performance at the same operating conditions as those just prior to the treat. These conditions were 140° C., 2.5 LHSV, 1:1 hexyl alcohol:cobalt formate water containing 0.55% cobalt, 20.67 MPa (3,000 psig), 800% excess syn gas (1:1 molar $H_2:CO$). Conversion of cobalt formate to hydrido cobalt carbonyl was measured to be 82.1%, which is significantly improved over the 66.8% observed just prior to the water/hydrogen treat.

The first order reversible kinetic expression indicated below has been used to calculate catalyst rate constant, k, as a function of time on feed. These results clearly show the improved performance resulting from the water/hydrogen wash.

$$k = LHSV * X_{Ae} * [-\ln * (1 - X_A/X_{Ae})]$$

where

LHSV = liquid hourly space velocity, vol. feed/hr/vol. of catalyst in reactor $X_{Ae}$ = fraction cobalt formate, $Co^{+2}$, converted at equilibrium $X_A$ = fraction cobalt formate, $Co^{+2}$, converted at time defined as 1/LHSV k's calculated from operation at 140° C. were adjusted to 120° by the following:

$$\ln (k_2/k_1) = E_A/R[(T_2 - T_1)/(T_1 * T_2)]$$

where
$k_2$ = k at 120° C.
$k_1$ = k at 140° C.
$T_2$ = 120° C. or 393° K.
$T_1$ = 140° C. or 413° K.
$E_A$ = Activation Energy, 10,250 cal/gm mole
R = Gas Constant, 1.987 gm. cal/gm mole °K.

| Days on Feed | k, 1/hr |
|---|---|
| 1.5 | 5.31 |
| 2.5 | 4.86 |
| 4.6 | 4.34 |
| 5.9 | 3.64 |
| 8.6 | 3.5 |
| 9.6 | 3.31 |
| 13.2 | 3.65 |
| 14.2 | 3.57 |
| 16.4 | 2.76 |
| 19.3 | 2.76 |
| 20.0 | 2.62 |
| 21.0 | 2.21 |
| 22.0 | 2.31 |
| 23.0 | 2.07 |
| 24.3 | 1.64 |
| Water Wash | |

| Days on Feed | k, 1/hr |
| --- | --- |
| 25.4 | 6.52 |
| 26.4 | 8.05 |

EXAMPLE TWO

A 2% Pd on activated carbon catalyst which was being used to convert an aqueous solution of cobalt formate to hydridocobalt carbonyl in the presence of an organic phase to extract the converted carbonyl, showed a decline in activity over a 27 day period. The history of the run follows.

The catalyst was started up with hexyl alcohol as the organic phase, and cobalt water containing 0.6 wt. % cobalt as cobalt formate at operating conditions of 5.0 LHSV, 120° C., 3,000 psig, 1:1 hexyl alcohol:cobalt water, 500% excess syn gas of 1:1 molar $H_2/CO$. After 2 days at these conditions, the catalyst activity was determined using a C10 hydrocarbon stream as the organic phase, designated as C10 LOF. Operating conditions were the same as with the hexyl alcohol except the liquid hourly space velocity was decreased to 2.5 and the feed cobalt water stream contained 0.9 wt. % cobalt. After measuring activity performance with this organic phase the catalyst was again tested with hexyl alcohol for 9 days. The organic phase was then changed to a stream composed nominally of 87% C9 aldehyde, 5% C9 alcohol and the remainder a mixture of C8 paraffin, C8 olefin and some heavier materials. This stream is designated C9 oxo product. Operating conditions were the same as with the C10 LOF stream except temperature was varied between 120° C. and 140° C. During 14 days of operation with the C9 oxo product, catalyst performance, as measured by a first order reversible rate constant, declined significantly. An activity check done with the C10 LOF feed, operating at the same conditions as before with this feed, confirmed the loss in activity. Following this activity check, a water/syn gas wash was conducted to restore the catalyst activity. Operating conditions for the wash step were 20.67 MPa (3000 psig) 2.5 LHSV, 150° C., and 200 GHSV of 1:1 molar $H_2/CO$. The wash step was carried out for approximately 16 hours. The catalyst was then tested with the C10 LOF organic feed at the same conditions as prior to the wash. The first order rate constant indicated complete restoration of catalyst activity.

The first order reversible kinetic expression indicated below has been used to calculate catalyst rate constant, k, as a function of time on feed. These results clearly show the improved performance resulting from the water/hydrogen wash.

$$k = LHSV * X_{Ae} * [-\ln * (1 - X_A/X_{Ae})]$$

where
LHSV = liquid hourly space velocity, vol. feed/hr/vol. of catalyst in reactor
$X_{Ae}$ = fraction cobalt formate, $Co^{+2}$, converted at equilibrium
$X_A$ = fraction cobalt formate, $Co^{+2}$, converted at time defined as 1/LHSV
k's calculated from operation at 140° C. with the C9 oxo product were adjusted to 120° C. using the following relationship:

$$\ln (k_2/k_1) = E_A/R [(T_2 - T_1)/(T_1 * T_2)]$$

where
$k_2$ = k at 120° C.
$k_1$ = k at 140° C.
$T_2$ = 120° C. or 393° K.
$R_1$ = 140° C. or 413° K.
$E_A$ = Activation Energy, 14,200 cal/gm mole
R = Gas Constant, 1.987 gm. cal/gm mole °K.

| Days on Feed | Organic Phase | k, 1/hr |
| --- | --- | --- |
| 1.0 | hexyl alcohol | 14.91 |
| 1.9 | " | 12.86 |
| 2.9 | C10 LOF | 2.2 |
| 4.5 | " | 2.2 |
| 5.5 | hexyl alcohol | 10.5 |
| 6.3 | " | 9.9 |
| 7.3 | " | 9.3 |
| 8.3 | " | 8.6 |
| 13.3 | " | 8.4 |
| 14.5 | C9 oxo product | 1.5 |
| 15.3 | " | 1.5 |
| 16.3 | " | 1.2 |
| 18.3 | " | 0.87 |
| 19.4 | " | 0.98 |
| 20.3 | " | 0.90 |
| 21.3 | " | 1.3 |
| 22.3 | " | 1.1 |
| 23.3 | " | 0.88 |
| 24.4 | " | 0.75 |
| 26.3 | " | 0.67 |
| 27.4 | C10 LOF Water Wash | 0.51 |
| 29.3 | C10 LOF | 2.4 |
| 30.1 | " | 2.4 |
| 32.4 | C9 oxo product | 2.2 |

EXAMPLE THREE

A 2% Pd on activated carbon catalyst was charged to a pilot unit reactor for evaluation as a cobalt formate preforming catalyst and feed streams were introduced to the catalyst without first activating the catalyst with a water/gas treat. After 8 days of operation, the catalyst was given a wash with water containing 1% formic acid and syn gas. The catalyst performance was again measured after the wash. A summary of the run follows:

The catalyst was started up with hexyl alcohol as the organic phase and cobalt water containing 0.6 wt. % cobalt as cobalt formate. Initial operating conditions were 5.0 LHSV, 120° C., 20.67 Mpa, (3000 psig), 1:1 hexyl alcohol:cobalt water, 500% excess syn gas of 1:1 molar ratio $H_2:CO$. After four days of operation at these conditions, the catalyst activity was determined using a C10 hydrocarbon stream as the organic phase, designated as C10 LOF. Operating conditions were the same as with the hexyl alcohol except the liquid hourly space velocity was decreased to 2.5. After five days of operation at these conditions, the catalyst was given a wash with syn gas and water containing 1% formic acid in order to activate or improve the activity of the catalyst. Operating conditions for the wash were 20.67 MPa (3000 psig), 4 LHSV water with 1% formic acid, 200 GHSV syn gas of 1:1 mole ratio $H_2:CO$, and 150° C. . The wash step was carried out for approximately 19 hours. The catalyst was then tested for activity performance with the C10 LOF organic feed and the cobalt water feed at the same conditions as prior to the wash. Improved preforming conversions were obtained after the wash as indicated below. Preforming conversion is calculated as:

100 * (moles Co$^{+2}$ in feed − moles Co$^{+2}$ in product) /moles Co$^{+2}$ in feed

| Days on Feed | Organic Phase | Preforming Conversion |
|---|---|---|
| 3.0 | hexyl alcohol | 70.0 |
| 4.0 | " | 67.9 |
| 7.0 | C10 LOF | 30.0 |
| 8.0 | " | 28.4 |
| 9.0 | " | 25.1 |
|  | Water Wash |  |
| 11.5 | C10 LOF | 40.0 |
| 13.8 | " | 43.0 |
| 14.7 | " | 42.3 |

EXAMPLE FOUR

A 2% Pd on activated carbon catalyst, which was being used to convert an aqueous solution of cobalt formate to hydrido cobalt carbonyl in the presence of an organic phase to extract the converted carbonyl, showed a decline in activity over a 23 day period. The history of the run follows.

The catalyst was started up with hexyl alcohol as the organic phase, and cobalt water containing 0.8 wt. % cobalt at operating conditions of 5.0 LHSV, 120° C., 20.67 MPa (3000 psig) 1:1 hexyl alcohol:cobalt water, 500% excess syn gas of 1:1 molar H$_2$/CO. After several days at these conditions, the catalyst activity was determined using a C10 hydrocarbon stream as the organic phase, designated as C10 LOF. Operating conditions were the same as with the hexyl alcohol except the liquid hourly space velocity was varied between 1.5 and 10 LHSV. After measuring activity performance with this organic phase, the catalyst was again tested with hexyl alcohol over a range of liquid hourly space velocities for 7 days. The organic phase was then changed back to the C10 LOF stream and an activity check was carried out at operating conditions of 2.5 LHSV, 120° C., 20.67 Pa (3000 psig), 1:1 C10 LOF:cobalt water, 500% excess syn gas of 1:1 molar H$_2$/CO. This activity check indicated the catalyst activity declined significantly as measured by a first order reversible rate constant. Following this activity check, a water/syn gas wash was conducted to restore the catalyst activity. Operating conditions for the wash step were 3 LHSV with water containing 1 wt. % formic acid, 150° C. and 200 GHSV of 1:1 molar H$_2$/CO. The wash step was carried out for 48 hours. The catalyst was then tested with the C10 LOF organic feed at the same conditions as prior to the wash and the catalyst activity was completely restored as indicated by the first order rate constant. A summary of the activity data is given below:

The first order reversible kinetic expression indicated below has been used to calculate catalyst rate constant, k, as a function of time on feed.

$$k = LHSV * X_{Ae} * [-\ln * (1 - X_A/X_{Ae})]$$

where
LHSV = liquid hourly space velocity, vol. feed / hr / vol. of catalyst in reactor
$X_{Ae}$ = fraction cobalt formate, Co$^{+2}$, converted at equilibrium
$X_A$ = fraction cobalt formate, Co$^{+2}$, converted at time defined as 1/LHSV A summary of catalyst activity, k, as a function of days on feed is given as follows:

| Days on Feed | Organic Phase | k, 1/hr at 120° C. |
|---|---|---|
| 3.0 | hexyl alcohol | 8.8 |
| 4.1 | " | 9.9 |
| 6.0 | C10 LOF | 1.9 |
| 7.0 | " | 2.0 |
| 9.0 | " | 1.7 |
| 11.1 | hexyl alcohol | 10.2 |
| 14.0 | " | 9.75 |
| 15.0 | " | 9.72 |
| 19.2 | " | 7.7 |
| 21.2 | C10 LOF | 0.85 |
| 23.2 | " | 0.63 |
|  | Water Wash |  |
| 25.3 | C10 LOF | 2.0 |
| 28.3 | " | 2.0 |

What is claimed is:

1. In the process for preparing oxo alcohols by the cobalt catalyzed hydroformylation of C$_2$ to C$_{17}$ linear or branched monoolefins with subsequent hydrogenation of the hydroformylation product, in which oxo process aqueous solutions of cobalt salts are converted to active hydrido cobalt carbonyl catalyst species in a preformer reactor, the preformer containing a preformer metal catalyst being a metal of Group IB or VIII of the Periodic Table, or a nonmetallic catalyst selected from the group consisting of activated carbon, ion exchange resins, silica alumina and zeolites, the improvement which comprises activating said preformer catalyst by treating it at a temperature of 120° C. to 170° C. and a pressure of about 13.78 MPa (2,000 psig) to 31.00 MPa (4,500 psig) with water or with a mixture of water and hydrogen or a mixture of water and syn gas for about 2-50 hours, whereby the conversion of said cobalt salts to said active cobalt catalyst species is improved when said salts are contacted with the treated preformer catalyst.

2. The process of claim 1 wherein the preformer catalyst is a Group IB or VIII metal.

3. The process of claim 2 wherein the metal is palladium.

4. The process of claim 3 wherein the palladium is present as 2 wt. % palladium on an activated carbon support.

5. The process of claim 1, 2, 3 or 4 wherein the aqueous solution of cobalt salt also contains an organic phase.

* * * * *